United States Patent [19]

Allgeier et al.

[11] 4,178,378

[45] Dec. 11, 1979

[54] ETHERIFIED TRIAZOLOBENZODIAZEPINE DERIVATIVES

[75] Inventors: Hans Allgeier, Lörrach-Haagen, Fed. Rep. of Germany; André Gagneux, Basel, Switzerland

[73] Assignee: Ciba-Geigy Corporation, Ardsley, N.Y.

[21] Appl. No.: 833,421

[22] Filed: Sep. 15, 1977

[30] Foreign Application Priority Data

Sep. 20, 1976 [LU] Luxembourg .......................... 75836

[51] Int. Cl.$^2$ .................... A61K 31/55; A61K 31/62; C07D 487/04
[52] U.S. Cl. ............................. 424/269; 260/239 BD; 260/244.4; 260/245.5; 260/340.9 R; 260/561 H; 424/232
[58] Field of Search .................... 260/308 R; 424/269, 424/232

[56] References Cited

U.S. PATENT DOCUMENTS

| 3,870,706 | 3/1975 | Allgeier et al. ................ 260/308 R |
| 3,946,032 | 3/1976 | Allgeier et al. ................ 260/308 R |

OTHER PUBLICATIONS

Allgeier et al. III, Chemical Abstracts, vol. 77, Abstract No. 88,554g (1972).

*Primary Examiner*—Alton D. Rollins

*Attorney, Agent, or Firm*—John J. Maitner

[57] ABSTRACT

Etherified diazepine derivatives of the formula

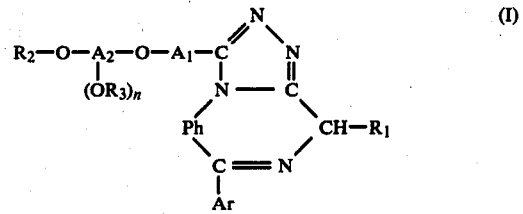

in which $R_1$ represents hydrogen or alkyl having up to 3 carbon atoms, $R_2$ and $R_3$ independently of one another each represent hydrogen or alkyl having up to 7 carbon atoms, or represent the partial formula $R_4$—(OCH$_2$—CH$_2$)$_m$, in which $R_4$ represents hydrogen or alkyl having up to 7 carbon atoms and m represents the number 1 to 3, $A_1$ represents alkylidene or alkylene having up to 3 carbon atoms, $A_2$, depending on the meaning of n, represents alkylene or alkanetriyl having up to 5 carbon atoms, no carbon atom in the radical $A_2$ being bonded to more than one oxygen atom, n represents the number 0 or 1, Ph represents substituted or unsubstituted 1,2-phenylene and Ar represents an aromatic radical, and their addition salts are manufactured according to methods known per se. They are useful in the treatment of states of epilepsy, stress and agitation.

32 Claims, No Drawings

ETHERIFIED TRIAZOLOBENZODIAZEPINE DERIVATIVES

The present invention relates to novel etherified diazepine derivatives and their acid addition salts having valuable pharmacological properties, processes for their preparation and also pharmaceutical compositions which contain the new substances as active compounds and the use of these compositions.

The etherified diazepine derivatives according to the invention are of the formula

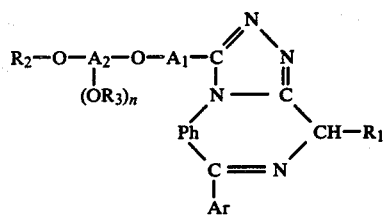

in which $R_1$ represents hydrogen or alkyl having up to 3 carbon atoms, $R_2$ and $R_3$ independently of one another each represent hydrogen or alkyl having up to 7 carbon atoms, or represent the partial formula $R_4$—(OCH$_2$—CH$_2$)$_m$, in which $R_4$ represents hydrogen or alkyl having up to 7 carbon atoms and m represents the number 1 to 3, $A_1$ represents alkylidene or alkylene having up to 3 carbon atoms, $A_2$, depending on the meaning of n, represents alkylene or alkanetriyl having up to 5 carbon atoms, no carbon atom in radical $A_2$ being bonded to more than one oxygen atom, n represents the number 0 or 1, Ph represents substituted or unsubstituted 1,2-phenylene and Ar represents an aromatic radical.

An aromatic radical Ar is preferably a carbocyclic, and especially a monocyclic, aryl radical and in particular is substituted or unsubstituted phenyl, and also a heterocyclic, such as an azacyclic, and especially a corresponding monocyclic hetero-aryl radical, such as substituted or unsubstituted pyridyl.

Substituents of 1,2-phenylene Ph and/or phenyl Ar and also pyridyl Ar are, especially, lower alkyl having up to and including 7 carbon atoms, lower alkoxy having up to and including 7 carbon atoms, halogen having an atomic number of up to and including 35, or trifluoromethyl.

A substituent of the radical Ph is preferably in the 4-position of the 1,2-phenylene radical, if the ring carbon atom of the 1,2-phenylene radical bonded to the ring nitrogen atom of the diazepine part is designated the 1-position (i.e. in the 8-position of the 4H-s-triazolo[4,3-a][1,4]benzodiazepine ring system), while substituents of a phenyl radical or of a pyridyl radical Ar can take up any position but, in particular, are in a position adjacent to the linking carbon atom.

Both above and below, the general concepts have the following meanings:

Lower alkyl represents, for example, methyl, ethyl, n-propyl or isopropyl and also n-butyl, isobutyl, tert.-butyl, n-pentyl, neopentyl, n-hexyl or n-heptyl.

Alkylidene or alkylene $A_1$ especially represents methylene or ethylidene, and also represents ethylene or 1,2- or 1,3-propylene.

Alkylene $A_2$ in particular represents ethylene and also represents 1,2- or 1,3-propylene or 1,4-butylene, while alkanetriyl (i.e. an alkylene radical which has an additional bond, if n in formula I represents 1) preferably represents 1,2,3-propanetriyl and also 1- or 2-methyl-1,2,3-propanetriyl or 1,2,4- or 1,3,4-butanetriyl.

Lower alkoxy especially represents methoxy and also ethoxy, n-propoxy, isopropoxy, n-butoxy, isobutoxy or tert.-butoxy.

Halogen having an atomic number of up to and including 35 is fluorine or bromine and, in particular, chlorine.

Salts of compounds of the formula I are acid addition salts, especially non-toxic acid addition salts which can be used pharmaceutically, such as those with inorganic acids, for example hydrochloric, hydrobromic, nitric, sulphuric or phosphoric acids, or with organic acids, such as organic carboxylic acids, for example acetic acid, propionic acid, glycollic acid, succinic acid, maleic acid, hydroxymaleic acid, methylmaleic acid, fumaric acid, malic acid, tartaric acid, citric acid, benzoic acid, cinnamic acid, mandelic acid, salicylic acid, 4-amino-salicylic acid, 2-phenoxybenzoic acid, 2-acetoxybenzoic acid, embonic acid, nicotinic acid or isonicotinic acid, or organic sulphonic acids, for example methanesulphonic acid, ethanesulphonic acid, 2-hydroxyethanesulphonic acid, ethane-1,2-disulphonic acid, benzenesulphonic acid, 4-methylbenzene-sulphonic acid or naphthalene-2-sulphonic acid, and also other acid addition salts which can be used, for example, as intermediates, for example for purifying the free compounds or in the preparation of other salts, and for characterisation, for example those with picric acid, picrolonic acid, flavianic acid, tungstophosphoric acid, molybdophosphoric acid, chloroplatinic acid, Reinecke's acid or perchloric acid.

The invention comprises the novel compounds of the formula I and also the salts in the form of mixtures of isomers or of single isomers, especially in the form of the racemates or antipodes if the compounds contain an asymmetric carbon atom.

The compounds of the formula I and also the corresponding salts possess valuable pharmacological properties. They have a sedative effect on the central nervous system and especially have an anticonvulsive and tranquillising action. The anticonvulsive activity can be demonstrated, for example, in the electric shock test on mice using doses of from about 0.6 mg/kg administered perorally, in the strychnine spasm test on mice using doses of from about 0.06 mg/kg administered perorally, in the pentetrazol test on mice using doses of from about 0.06 mg/kg administered perorally and in the picrotoxin test using doses of from about 0.03 mg/kg administered perorally. The tranquillising activity can be seen from the action in the said pentetrazol test, but can also be demonstrated with the aid of observation tests with doses of about 0.3 mg/kg. The said types of action and further types of action which can be detected with the aid of selected standard tests [c.f. W. Theobald and H. A. Kunz, Arzneimittelforsch., Volume 13, page 122 (1963) and also W. Theobald et al., Arzneimittelforsch., Volume 17, page 561 (1967)], characterise the compounds of the formula I and their salts as active compounds for anticonvulsants and tranquillisers which, in accordance with their particularly strong action in the electric shock test, can be used, in particular, for the treatment of states of epilepsy, but also of states of stress and agitation.

The invention relates in particular to compounds of the formula I in which $R_1$ represents hydrogen, $R_2$ and $R_3$ each independently of one another represent hydrogen or alkyl having up to 3 carbon atoms, for example methyl, or $R_2$ represents the partial formula $R_4$—(OCH$_2$—CH$_2$)$_m$—, in which $R_4$ represents alkyl having up to 3 carbon atoms, for example methyl, $A_1$ represents methylene, n represents 0 or 1, $A_2$ represents ethylene if n represents 0, or represents 1,2,3-propanetriyl if n represents 1, Ph represents 1,2-phenylene, which is preferably substituted by halogen, especially chlorine, halogen being, in particular, in the 4-position relative to the ring carbon atom of the 1,2-phenylene radical which is linked to the ring carbon atom of the diazepine radical, and Ar represents phenyl which is unsubstituted or substituted by halogen, such as fluorine or chlorine, halogen preferably being in the 2-position, or salts thereof, such as acid addition salts thereof, preferably acid addition salts thereof which can be used pharmaceutically.

The invention relates especially to 1-(2-R$_2$O-ethoxymethyl)- and also 1-(2,3-dihydroxy-propoxy-methyl)-6-(2-R-phenyl)-8-chloro-4H-s-triazolo[4,3-a][1,4]benzodiazepines, in which $R_2$ represents hydrogen or methyl and R represents hydrogen, fluorine or chlorine, or salts thereof, such as acid addition salts thereof, preferably corresponding salts thereof which can be used pharmaceutically.

The invention relates in particular to the compounds of the formula I mentioned in the examples and also to salts thereof, such as acid addition salts thereof, preferably acid addition salts thereof which can be used pharmaceutically.

The compounds of the formula I can be prepared in a manner which is known per se.

Thus, they are obtained, for example, when a compound of the formula

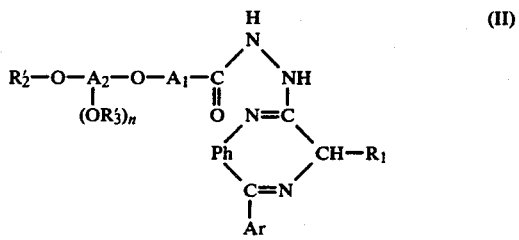

(II)

in which $R_2'$ and $R_3'$ have the meanings defined for $R_2$ and $R_3$ respectively, with the exception of hydrogen, or each individually represent, or together represent, a detachable radical which can be replaced by hydrogen, or a tautomer of this compound is cyclised and, in a compound of the formula

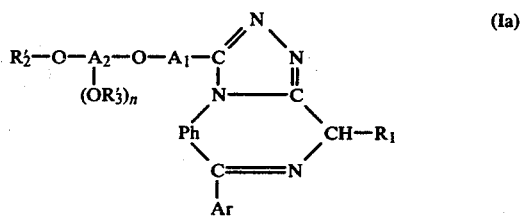

(Ia)

which is obtainable according to the process and in which $R_2'$ and/or $R_3'$ differ from $R_2$ and/or $R_3$ and each individually represent, or together represent, a detachable radical which can be replaced by hydrogen, a radical of this type is replaced by hydrogen and, if desired, a resulting compound of the formula I is converted into another compound of the formula I and/or, if desired, a resulting free compound is converted into a salt, or a resulting salt is converted into the free compound or into another salt, and/or a resulting mixture of isomers is separated into the individual isomers.

A tautomer of the starting material of the formula II is, in particular, the corresponding hydrazono compound of the formula

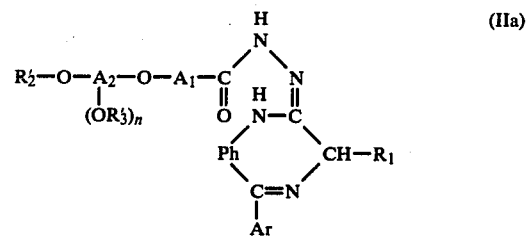

(IIa)

but can also be any of the other possible tautomeric forms.

In a starting material of the formula II, or in a corresponding tautomer, detachable radicals $R_2'$ and/or $R_3'$ are, in particular, hydroxyl-protective groups detachable by solvolysis, for example hydrolysis, alcoholysis or acidolysis, and also by reduction, for example by hydrogenolysis, for example corresponding radicals which esterify or etherify a hydroxyl group. Groups detachable by solvolysis are, in particular, acyl groups, which preferably are derived from organic carboxylic acids or from half-derivatives, for example half-esters, of carbonic acid; such radicals are, for example, lower alkanoyl which is unsubstituted or substituted, for example by halogen, such as fluorine or chlorine, such as acetyl or propionyl, or benzoyl and also substituted or unsubstituted lower alkoxycarbonyl, for example ethoxycarbonyl or tert.-butoxycarbonyl, or substituted or unsubstituted phenyl-lower alkoxycarbonyl, for example benzhydryloxycarbonyl, and also suitable etherifying groups, such as 2-oxacycloalkyl, for example 2-tetrahydropyranyl. Radicals detachable by reduction are, in particular, α-aryl-lower alkyl groups, such as benzyl which is unsubstituted or substituted, for example by lower alkoxy, such as methoxy, or nitro, and also suitably substituted lower alkoxycarbonyl, especially lower alkoxycarbonyl containing halogen, such as 2,2,2-trichloroethoxycarbonyl.

A detachable radical formed by the two radicals $R_2'$ and $R_3'$ conjointly is, especially, an ylidene group detachable by solvolysis, for example by hydrolysis or alcoholysis, especially lower alkylidene, for example isopropylidene, or cycloalkylidene, for example cyclohexylidene.

The starting material of the formula II, or a tautomer thereof, which can be cyclised in situ, i.e. under the conditions of its preparation, is preferably converted into the desired compound of the formula I at elevated temperature, for example in a range of about 80° C. to about 220° C. The reaction is carried out in the absence, but preferably in the presence, of a solvent or diluent, especially of a higher-boiling organic solvent or diluent, such as of a corresponding hydrocarbon, halogenohydrocarbon, ether, amide, sulphoxide or alcohol, for example toluene, xylene, chlorobenzene, diethylene glycol dimethyl ether or diethylene glycol diethyl ether, N,N,N',N',N'',N''-hexamethylphosphoric acid amide, N,N-dimethylacetamide or n-butanol, or of a corresponding mixture, if necessary in a closed vessel under pressure and/or in an inert gas atmosphere, for example a nitrogen atmosphere.

In a compound of the formula Ia, obtainable according to the process, the groups which do not have the meanings defined for $R_2$ and/or $R_3$ are detached and replaced by hydrogen. Groups $R_2$ and/or $R_3$ detachable by solvolysis can, inter alia, be detached, and replaced by hydrogen, by hydrolysis, for example by treatment with water in the presence of a basic or acid hydrolysing agent, such as of an alkali metal hydroxide, for example sodium hydroxide or potassium hydroxide, or of a mineral acid, for example hydrochloric acid, or a strong organic sulphonic acid, for example 4-methylphenylsulphonic acid, by alcoholysis, for example by treatment with a lower alkanol, such as methanol or ethanol, in the presence of a suitable catalyst, such as of a corresponding alcoholate, for example of an alkali metal lower alkanoate, for example a sodium lower alkanoate or potassium lower alkanoate, or of a Lewis acid, for example boron trifluoride (for example in the form of the diethyl etherate), or by acidolysis, for example by treatment with a strong organic carboxylic acid, such as formic acid or trifluoroacetic acid. Furthermore, an α-aryl-lower alkyl group, for example a benzyl group, present as $R_2'$ and/or $R_3'$, can be detached, and replaced by hydrogen, by hydrogenolysis, for example by treatment with hydrogen in the presence of a suitable catalyst, and a 2-halogeno-lower alkoxycarbonyl group, for example 2,2,2-trichloroethoxycarbonyl, can be detached, and replaced by hydrogen, by chemical reduction, such as by treatment with a reducing metal, for example zinc, in the presence of a hydrogen donor, for example aqueous acetic acid. These reactions are carried out in a manner which is known per se.

The starting materials, which, if desired, can be formed in situ and cyclised directly, under the conditions of their preparation, to give the desired compounds of the formula I or Ia, can be obtained, for example, when a compound of the formula

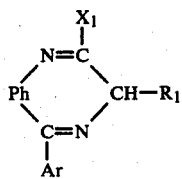

(III)

in which $X_1$ represents a suitable leaving group, for example free or etherified mercapto, such as mercapto or lower alkylthio, for example methylthio, etherified hydroxyl, such as lower alkoxy, for example methoxy, cyano, di-tert.-aminophosphinyloxy, for example dimorpholino-phosphinyloxy, or unsubstituted, monosubstituted or disubstituted amino, such as lower alkylamino, for example methylamino, aryl-lower alkylamino, for example benzylamino, di-lower alkylamino, for example dimethylamino, or N-lower alkyl-N-nitroso-amino, for example N-methyl-N-nitroso-amino, is reacted with a hydrazide of the formula

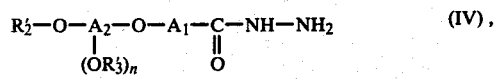

(IV), the reaction preferably being carried out at elevated temperature, for example in a range from about 80° C. to about 220° C., and, if desired or necessary, in the presence of a suitable solvent or diluent, such as one of those mentioned above, in a closed vessel under pressure and/or in an inert gas atmosphere.

Furthermore, it is possible, starting from a compound of the formula III in which $X_1$ represents hydrazino, to react this with a reactive derivative of an acid of the formula

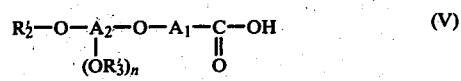

(V)

especially with an anhydride or a halide, for example the chloride, and thus to obtain a starting material of the formula II and, under suitable reaction conditions, such as under elevated temperature, to obtain compounds of the formula I or Ia directly. This reaction can be carried out, for example, in the presence of a suitable acid-binding agent, such as triethylamine or pyridine.

If the starting materials are formed under mild conditions, for example at an only moderately elevated temperature, and/or using a suitable intermediate of the formula III, an intermediate of the formula II can then be isolated. Usually, however, the cyclisation according to the invention is carried out without isolating the starting material of the formula II.

The intermediates of the formula III are known or can be prepared in a manner which is known per se. Attention is drawn, in this connection, to, for example, Sternbach and Reeder, J. Org. Chem., Volume 26, page 1,111 (1961); Bell et al., J. Med. Chem., Volume 5, page 63 (1962); Archer and Sternbach, J. Org. Chem., Volume 29, page 231 (1964); Coffen et al., J. Org. Chem., Volume 39, page 167 (1974) and Walser et al., J. Het. Chem., Volume 11, page 619 (1974); and also German Offenlegungsschriften Nos. 1,933,986, 2,012,190, 2,114,441, 2,335,281, 2,540,522 and 2,540,586 and British Patent Specification No. 1,023,793; and also to Netherlands Published Specification No. 69.16543 and Belgian Patent Specification No. 741,317. Thus, for example, compounds of the formula III in which $X_1$ represents hydrazino can be obtained by reacting a corresponding compound of the formula III in which $X_1$ represents, for example, substituted or unsubstituted amino, mercapto, methylthio or a methoxy group, preferably in a lower alkanol, for example methanol or ethanol, to which 1–3% of acetic acid are added if appropriate, with hydrazine hydrate, at room temperature up to the boiling point of the solvent. Compounds of the formula V and their reactive derivatives, and also their hydrazides of the formula IV, are known or can be prepared in a manner which is known per se; the hydrazides, for example, can be prepared from the corresponding esters.

The compounds of the formula I can also be obtained when a compound of the formula

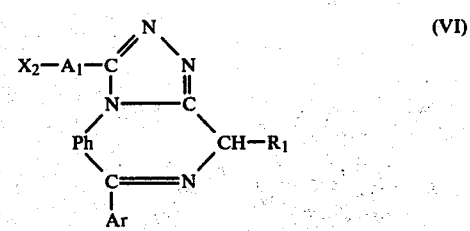

(VI)

is reacted with a compound of the formula

in which formulae one of the groups $X_2$ and $X_3$ represents a reactive, esterified hydroxyl group and the other represents a hydroxyl group present in the form of an alcoholate, and $R_2''$ and $R_3''$ have the meanings defined for $R_2$ and $R_3$ respectively or each individually represent, or together represent, a detachable radical which can be replaced by hydrogen, and, in a compound of the formula

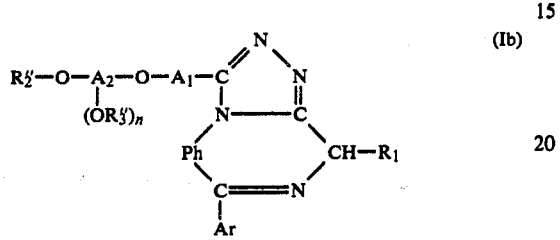

which is obtainable according to the process and in which $R_2''$ and/or $R_3''$ differ from $R_2$ and/or $R_3$ and each individually represent, or together represent, a detachable radical which can be replaced by hydrogen, a radical of this type is replaced by hydrogen and, if desired, the abovementioned additional process steps are carried out.

A reactive, esterified hydroxyl group $X_2$ or $X_3$ is a hydroxyl group esterified by a strong inorganic or organic acid and in particular represents halogen having an atomic number greater than 9, for example chlorine or bromine, or organic sulphonyloxy, such as lower alkylsulphonyloxy, for example methylsulphonyloxy, or arylsulphonyloxy, for example 4-methylphenylsulphonyloxy or 4-bromophenylsulphonyloxy. A hydroxyl group in the form of an alcoholate is, in particular, alkali metal-oxy, such as sodium-oxy or potassium-oxy.

Detachable radicals $R_2''$ and/or $R_3''$ are, for example, the radicals mentioned above for the groups $R_2'$ and/or $R_3'$.

The above reaction can be carried out according to methods which are known per se, usually in the presence of a solvent or diluent, for example benzene, dimethylformamide, N,N,N',N',N'',N''-hexamethyl-phosphoric acid triamide, dimethylformamide or acetonitrile, if necessary with cooling or preferably with warming, for example in a temperature range of about 10° C. to about 120° C., in a closed vessel and/or in an inert gas atmosphere.

In a compound of the formula Ib, detachable radicals $R_2''$ and/or $R_3''$, which differ from $R_2$ and/or $R_3$ and can be replaced by hydrogen, are detached, and replaced by hydrogen, in a manner which is known per se, for example as described above for the radicals $R_2'$ and/or $R_3'$ in a compound of the formula Ia.

The starting materials of the formulae VI and VII are known or can be prepared in a manner which is known per se. Thus, for example, the compounds of the formula VI in which $X_2$ represents a hydroxyl group present in the form of an alcoholate, for example in the form of an alkali metal-oxy group, are obtained from the corresponding hydroxy compounds, for example the hydroxy compounds described in German Offenlegungsschrift No. 2,156,472, for example by treatment with a metal, for example an alkali metal, or a suitable derivative thereof. Compounds of the formula VI in which $X_2$ represents a hydroxyl group esterified by a strong acid are known, inter alia, from German Offenlegungsschriften No. 2,201210 (for example the mesyloxy compounds) and No. 2,159,242 (for example halogeno compounds, especially bromo compounds).

The compounds of the formula I can also be obtained when a compound of the formula

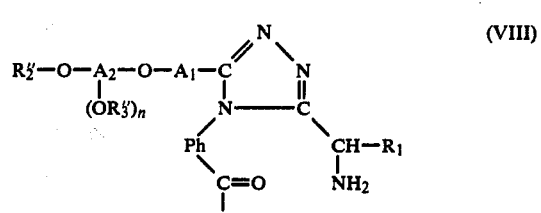

in which $R_2''$ and $R_3''$ are as defined above, is cyclised and, in a compound of the formula Ib which is obtainable according to the process and in which n represents 0 and $R_2''$ and/or $R_3''$ differ from $R_2$ and/or $R_3$ and each individually represent, or together represent, a detachable radical which can be replaced by hydrogen, such a radical is replaced by hydrogen, and/or, if desired, the abovementioned additional process steps are carried out.

The above cyclisation of a starting material of the formula VIII, which usually takes place in situ, i.e. under the conditions for the preparation of the starting material, is carried out by methods which are known per se, preferably in the presence of a suitable solvent or diluent, such as of an ether, alcohol, amide or unsubstituted or halogenated hydrocarbon, and with cooling, at room temperature or, preferably, with warming, for example within a temperature range of about 20° C. to about 120° C., and, if necessary, in a closed vessel and/or in an inert gas atmosphere.

The starting materials of the formula VIII, which usually are cyclised under the reaction conditions for their preparation, i.e. without being isolated, to give the compounds of the formula I or Ib, can be prepared in a manner which is known per se. Thus, a compound of the formula H$_2$H—Ph—C(=O)—Ar (c.f., inter alia, Chattaway, J. Chem. Soc., Volume 85, page 344 (1904) or Sternbach et al., J. Org. Chem., Volume 26, page 4,488 (1961) and Volume 27, page 3,781–3,788 (1962)) can be reacted with an acid of the formula

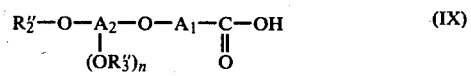

or preferably with a suitable reactive derivative thereof, such as an ester, for example a lower alkyl ester, an anhydride or a halide, for example the chloride, usually in the presence of a condensing agent, preferably a basic condensing agent, for example triethylamine, ethyldiisopropyl-amine, pyridine or 2-methyl-imidazole, or with an ortho-ester, such as a corresponding ortho-lower alkyl ester, for example orthomethyl ester or orthoethyl ester, of the above acid of the formula IX in the presence of an acid condensing agent, such as an acid, for example hydrochloric acid, acetic acid or 4- methylphenylsulphonic acid. This gives an intermediate of the formula

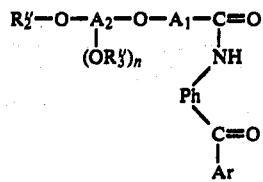

or, when an ortho-ester of an acid of the formula IX is used, an intermediate of the formula

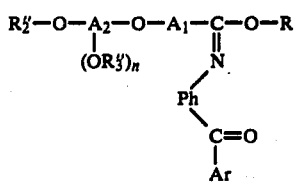

in which R represents the esterifying radical present in the ortho-ester used of an acid of the formula IX, such as lower alkyl, for example methyl or ethyl. If a compound of the formula Xa or Xb is reacted with hydrazine, which can be in the form of the hydrate, and, if necessary, in the presence of an acid condensing agent, such as an inorganic or organic acid, a compound of the formula

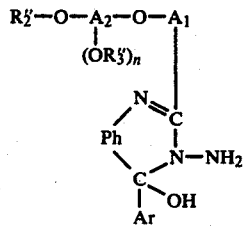

forms and this can be acylated by reaction with an acid of the formula

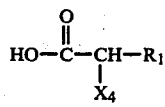

in which $X_4$ represents a reactive esterified hydroxyl group, especially halogen, for example chlorine or bromine, or preferably with a suitable reactive derivative thereof, such as an anhydride or an acid halide, for example an acid chloride thereof, preferably in the presence of an acid-binding agent. The acylation product, which is preferably a monoacyl compound of the formula

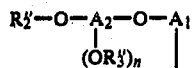
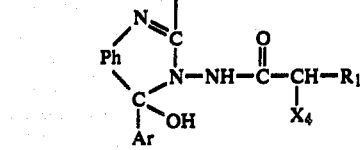

or a mixture thereof with a di-acylated and/or poly-acylated product, is converted, in a weakly acid medium, for example in the presence of an aliphatic carboxylic acid, such as an unsubstituted or halogenated lower alkanecarboxylic acid, for example formic acid, acetic acid, chloroacetic acid or dichloroacetic acid, or of an aromatic carboxylic acid, for example benzoic acid, salicyclic acid, phenylacetic acid or hydrocinnamic acid, and, if necessary, in a suitable solvent or diluent, with warming, for example in a temperature range of about 50° C. to about 150° C., into a compound of the formula

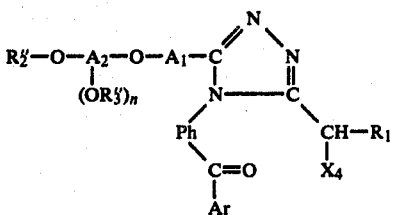

In this compound, the reactive esterified hydroxyl group $X_4$ can be converted into the amino group of the starting material of the formula VIII in a manner which is known per se, for example by reaction with ammonia or a suitable ammonia donor, for example hexamethylenetetramine, by treatment with an alkali metal azide and subsequent reduction (for example with triphenylphosphine, tin-II chloride or catalytically activated hydrogen) or by reaction with a metal compound, for example an alkali metal compound, of an amide or imide, for example of phthalimide or succinimide, and subsequent solvolysis (for example with hydrazine hydrate or an alcoholic-aqueous solution of an alkali metal hydroxide). The cyclisation, according to the process, to give a desired compound of the formula I or Ib can take place at the same time, under the conditions for the formation of the amino group.

A compound of the formula I, obtainable according to the process, can be converted into another compound of the formula I by methods which are known per se.

Thus, for example, in a compound of the formula I in which $R_2$ and/or $R_3$ represent hydrogen, the free hydroxyl group or groups can be converted into a corresponding alkoxy group or corresponding alkoxy groups, for example by treating compounds of the formula I in which $R_2O-$ and/or $R_3O-$ represent a hydroxyl group or hydroxyl groups present in the form of an alcoholate, for example in the form of an alkali metaloxy group, with a reactive ester of an alkanol having up to and including 7 carbon atoms, such as a corresponding alkyl halide.

Furthermore, in a compound of the formula I in which $R_2$ and/or $R_3$ represent hydrogen, the free hydroxyl group or groups can be converted into a reactive esterified hydroxyl group or reactive esterified hydroxyl groups, for example halogen, such as chlorine, for example by treatment with a suitable halogenating agent, such as thionyl chloride, and the intermediate thus obtainable can be reacted with a metal alkanolate having up to and including 7 carbon atoms, for example a corresponding alkali metal alkanolate, and compounds of the formula I in which $R_2$ and/or $R_3$ represent alkyl having up to and including 7 carbon atoms can thus be obtained.

Resulting free compounds of the formula I can be converted into their acid addition salts in a manner which is known per se, for example by reacting a solution thereof in a suitable solvent or solvent mixture with an acid, such as one of the abovementioned acids, or with a solution thereof, or with a suitable anion exchanger.

Resulting salts can be converted into the free compounds of the formula I in a manner which is known per se, for example by treatment with a base, such as a metal hydroxide, for example sodium hydroxide, potassium hydroxide or calcium hydroxide, a metal carbonate, for example sodium carbonate or bicarbonate, potassium carbonate or bicarbonate or calcium carbonate or bicarbonate, or ammonia, and also by treatment with a suitable anion exchanger.

Resulting salts can be converted into other salts in a manner which is known per se, for example by treatment with an anion exchanger or by treating a salt of an inorganic acid with a suitable metal salt, such as a sodium salt, barium salt or silver salt, of an acid, in a solvent in which an inorganic salt which forms is insoluble and thus separates out of the reaction mixture.

The compounds of the formula I and their salts can also be obtained in the form of their hydrates or can, for example, incorporate the solvent used for crystallisation.

Because of the close relationship between the novel compounds in the free form and in the form of their salts, the free compounds or their salts in the preceding and following text, are, where appropriate, also to be understood as meaning the corresponding salts and, respectively, free compounds in respect of general sense and intended use.

Resulting mixtures of isomers can be separated into the individual isomers in a manner which is known per se. Thus, racemates can be converted into the antipodes, for example by crystallisation from optically active solvents or, preferably in the presence of a suitable solvent, by treating them with optically active acids and separating the mixture of the diastereomeric salts. Optically active acids suitable for this purpose are, inter alia, the optically active forms of organic carboxylic or sulphonic acids, for example tartaric acid, malic acid, mandelic acid, camphor-10-sulphonic acid or quinic acid. The resulting diastereomeric salts can be converted into other salts or into the free and optically active bases, for example by the methods described above.

The invention also relates to those embodiments of the process in which a compound obtainable as an intermediate at any stage of the process is used as the starting material and the missing process steps are carried out, or in which a starting material is formed under the reaction conditions or is used in the form of a derivative thereof, if appropriate in the form of a salt.

The starting materials used in the process of the present invention are preferably those which result in the compounds described initially as being particularly valuable.

The present invention also relates to pharmaceutical formulations which contain compounds of the formula I or salts thereof which can be used pharmaceutically. The pharmaceutical formulations according to the invention are those for enteral, such as oral or rectal, and also parenteral administration and contain the pharmacological active compound on its own or together with an excipient which can be used pharmaceutically. The dosage of the active compound depends on the species of warm-blooded animal, the age and the state of health of the individual and also on the mode of administration. The daily doses to be administered to warm-blooded animals are between about 0.3 mg/kg and about 2 mg/kg and for warm-blooded animals weighing about 70 kg are preferably between about 0.05 and 4.0 mg/kg.

The novel pharmaceutical formulations contain from about 5% to about 95%, and preferably from about 10% to about 90%, of the active compound; pharmaceutical formulations, according to the invention, in the form of dosage units are, for example, dragées, tablets, capsules, suppositories or ampoules.

The pharmaceutical formulations of the present invention are prepared in a manner which is known per se, for example by means of conventional mixing, granulating, dragée-making, dissolving or lyophilising processes. Thus, pharmaceutical formulations for oral use can be obtained by combining the active compound with solid excipients, granulating a resulting mixture if desired and processing the mixture or granules, after adding suitable auxiliaries if desired or necessary, to give tablets or dragée cores.

Suitable excipients are, especially, fillers, such as sugars, for example lactose or sucrose, mannitol or sorbitol, cellulose formulations and/or calcium phosphates, for example tricalcium phosphate or calcium hydrogen phosphate, as well as binders, such as starch pastes using, for example, maize starch, wheat starch, rice starch or potato starch, gelatine, tragacanth, methylcellulose, hydroxypropyl-methylcellulose, sodium carboxymethylcellulose and/or polyvinylpyrrolidone, and/or, if desired, disintegrating agents, such as the above-mentioned starches, and also carboxymethylstarch, cross-linked polyvinylpyrrolidone, agar or alginic acid or a salt thereof, such as sodium alginate. Auxiliaries are, in particular, flow control agents and lubricants, for example silica, talc, stearic acid or salts thereof, such as magnesium stearate or calcium stearate, and/or polyethylene glycol. Dragée cores are provided with suitable coatings which, if desired, are resistant to gastric juices, and for this purpose, inter alia, concentrated sugar solutions, which can contain gum arabic, talc, polyvinylpyrrolidone, polyethylene glycol and/or titanium dioxide, lacquer solutions in suitable organic solvents or solvent mixtures or, in order to produce coatings resistant to gastric juices, solutions of suitable cellulose formulations, such as acetylcellulose phthalate or hydroxypropylmethylcellulose phthalate, are used. Dyes or pigments can be added to the tablets or dragée coatings, for example for identification or in order to characterise different doses of active compound.

Other pharmaceutical formulations which can be used orally are push-fit capsules made of gelatine, as well as soft, sealed capsules made of gelatine and a plasticiser, such as glycerol or sorbitol. The push-fit capsules can contain the active compound in the form of granules, for example mixed with fillers, such as lactose, binders, such as starches, and/or lubricants, such as talc or magnesium stearate, and can contain stabilisers. In soft capsules, the active compound is preferably dissolved or suspended in suitable liquids, such as fatty oils, liquid paraffin or liquid polyethylene glycols, it also being possible to add stabilisers.

Possible pharmaceutical formulations which can be used rectally are, for example, suppositories, which consist of a combination of the active compound with a suppository base. Suitable suppository bases are, for example, natural or synthetic triglycerides, paraffin hydrocarbons, polyethylene glycols or higher alkanols. In addition, it is also possible to use gelatine rectal capsules which consist of a combination of the active compound with a base; bases which can be used are, for example, liquid triglycerides, polyethylene glycols or paraffin hydrocarbons.

Formulations suitable for parenteral administration are, in particular, aqueous solutions of an active compound in the water-soluble form, for example of a water-soluble salt, and also suspensions of the active compound, such as corresponding oily injection suspensions, in which case suitable lipophilic solvents or vehicles, such as fatty oils, for example sesame oil, or synthetic fatty acid esters, for example ethyl oleate or triglycerides, are used, or aqueous injection suspensions which contain substances which increase the viscosity, for example sodium carboxymethylcellulose, sorbitol and/or dextran, and can also contain stabilisers.

The invention also comprises the use of the novel compounds of the formula I, or salts thereof, preferably in the form of pharmaceutical formulations.

The examples which follow illustrate the invention described above; however, they are not intended to restrict the scope of the invention in any way. Temperatures are given in degrees centigrade.

EXAMPLE 1

A solution of 17.4 g of 7-chloro-2-methylthio-5-phenyl-3H-1,4-benzodiazepine (c.f. G. A. Archer et al., J. Org. Chem., Volume 29, page 231 (1964)) and 13 g of 2-[(2,2-dimethyl-1,3-dioxolan-4-yl)-methoxy]-acetic acid hydrazide in 150 ml of absolute hexamethylphosphoric acid triamide is heated at 140° for 21 hours. The solvent is then distilled off under reduced pressure and the residue is partitioned between ethyl acetate and water. The organic phase is separated off, washed with a saturated aqueous solution of sodium chloride, dried over magnesium sulphate and evaporated. Chromatography on silica gel (particle size 0.063–0.2 mm) using a 4:1 mixture of ethyl acetate and isopropanol as the eluant, gives 8-chloro-1-[(2,2-dimethyl-1,3-dioxolan-4-yl)-methoxymethyl]-6-phenyl-4H-s-triazolo[4,3-a][1,4]benzodiazepine, which is further processed as the crude product.

(a) A solution of 20 g of 8-chloro-1-[(2,2-dimethyl-1,3-dioxolan-4-yl)-methoxymethyl]-6-phenyl-4H-s-triazolo[4,3-a][1,4]benzodiazepine in 200 ml of methanol and 9 ml of boron trifluoride-diethyl etherate is stirred at 25° for 26 hours. The reaction mixture is partitioned between methylene chloride and water; the organic phase is separated off, washed with water, dried over magnesium sulphate and evaporated. Crystallisation from ethyl acetate gives 8-chloro-1-(2,3-dihydroxy-propoxy-methyl)-6-phenyl-4H-s-triazolo[4,3-a][1,4]benzodiazepine, melting point 130°–134°.

(b) A solution of 16 g of 8-chloro-1-[(2,2-dimethyl-1,3-dioxolan-4-yl)-methoxymethyl]-6-phenyl-4H-s-triazolo[4,3-a][1,4]benzodiazepine in 100 ml of ethanol and 110 ml of 0.1 N hydrochloric acid is stirred at 25° for 48 hours. The reaction mixture is neutralised with a concentrated aqueous solution of ammonia and evaporated under reduced pressure. The residue is partitioned between methylene chloride and water. The organic phase is separated off, washed with water, dried over magnesium sulphate and evaporated. Crystallisation from ethyl acetate gives the desired 8-chloro-1-(2,3-dihydroxypropoxy-methyl)-6-phenyl-4H-s-triazolo[4,3-a][1,4]benzodiazepine, melting point 130°–134°.

2-[2,2-Dimethyl-1,3-dioxolan-4-yl)-methoxy]-acetic acid hydrazide, which is used as the starting material, can be prepared as follows:

A mixture of 21.5 g of ethyl 2-[(2,2-dimethyl-1,3-dioxolan-4-yl)-methoxy]-acetate (for example prepared according to J. Chem. Soc., (1965), page 2,968) and 10 g of hydrazine hydrate in 250 ml of ethanol is left to stand for 20 hours at 25°. The colourless solution is evaporated under reduced pressure and 2-[(2,2-dimethyl-1,3-dioxolan-4-yl)-methoxy]-acetic acid hydrazide, which is thus obtained, is reacted further direct.

In an analogous manner, using suitable starting materials, it is possible, for example, to obtain the following compounds: 8-chloro-1-(2,3-dihydroxy-propoxymethyl)-6-(2-fluorophenyl)-4H-s-triazolo[4,3-a][1,4]benzodiazepine, from 16.0 g of 7-chloro-5-(2-fluorophenyl)-2-methylthio-3H-1,4-benzodiazepine and 2-[(2,2-dimethyl-1,3-dioxolan-4-yl)-methoxy]-acetic acid hydrazide; 8-chloro-1-(2-methoxy-ethoxy-methyl)-6-phenyl-4H-s-triazolo[4,3-a][1,4]benzodiazepine, from 15.0 g of 7-chloro-2-methylthio-5-phenyl-3H-1,4-benzodiazepine and 2-(2-methoxy-ethoxy)-acetic acid hydrazide; 8-chloro-6-(2-chlorophenyl)-1-(2-methoxy-ethoxy-methyl)-4H-s-triazolo[4,3-a][1,4]benzodiazepine, from 17.6 g of 7-chloro-5-(2-chlorophenyl)-2-methylthio-3H-1,4-benzodiazepine and 2-(2-methoxy-ethoxy)-acetic acid hydrazide; and 8-chloro-6-(2-fluorophenyl)-1-(2-methoxy-ethoxy-methyl)-4H-s-triazolo[4,3-a][1,4]benzodiazepine, from 16 g of 7-chloro-5-(2-fluorophenyl)-2-methylthio-3H-1,4-benzodiazepine and 2-(2-methoxy-ethoxy)-acetic acid hydrazide.

EXAMPLE 2

A solution, prepared at 70°, of 2.83 g of sodium in 200 ml of ethylene glycol is treated with 24.8 g of 8-chloro-1-methylsulphonyloxymethyl-6-phenyl-4H-s-triazolo[4,3-a][1,4]benzodiazepine (c.f. German Offenlegungsschrift 2,201,210, Example 1) and the mixture is stirred for 6 hours at 70°. The reaction mixture is partitioned between ethyl acetate and water. The organic phase is separated off, washed with a saturated aqueous solution of sodium chloride, dried over magnesium sulphate and evaporated. Crystallisation from ethyl acetate gives 8-chloro-1-(2-hydroxyethoxy-methyl)-6-phenyl-4H-s-triazolo[4,3-a][1,4]benzodiazepine, melting point 162°–164°.

In an analogous manner it is possible, using suitable starting materials, to obtain, for example, the following compounds: 8-chloro-6-(2-chlorophenyl)-1-(2-hydroxy-ethoxy-methyl)-4H-s-triazolo[4,3-a][1,4]benzodiazepine, from 8-chloro-6-(2-chlorophenyl)-1-methylsulphonyloxy-methyl-4H-s-triazolo[4,3-a][1,4]benzodiazepine; and 8-chloro-6-(2-fluorophenyl)-1-(2-hydroxy-ethoxy-methyl)-4H-s-triazolo[4,3-a][1,4]benzodiazepine, from 8-chloro-6-(2-fluorophenyl)-1-methylsulphonyloxy-methyl-4H-s-triazolo[4,3-a][1,4]benzodiazepine.

EXAMPLE 3

A solution, prepared at 50°, of 4.6 g of sodium in 120 ml of 2,2-dimethyl-4-hydroxymethyl-1,3-dioxolane is treated with 37 g of crude 8-chloro-1-methylsulphonyloxymethyl-6-phenyl-4H-s-triazolo[4,3-a][1,4]benzodiazepine and the mixture is stirred for 2 hours at 50°. The reaction mixture is partitioned between ethyl acetate and water; the organic phase is separated off, washed with a saturated aqueous solution of sodium chloride, dried over magnesium sulphate and evaporated. Chromatography on silica gel (particle size 0.063–0.2 mm), using a 7:2 mixture of ethyl acetate and isopropanol as the eluant, gives 8-chloro-1-[(2,2-dimethyl-1,3-dioxolan-4-yl)-methoxymethyl]-6-phenyl-4H-s-triazolo[4,3-a][1,4]benzodiazepine which is further processed as the crude product and is converted, for example by the process described in Example 1, into 8-chloro-1-(2,3-dihydroxy-propoxy-methyl)-6-phenyl-4H-s-triazolo[4,3-a][1,4]benzodiazepine, which has a melting point of 130°–134° after recrystallisation from ethyl acetate.

EXAMPLE 4

A solution of 7.0 g of 7-chloro-2-mercapto-5-phenyl-3H-1,4-benzodiazepine [c.f. Archer and Sternbach, J. Org. Chem., Volume 29, page 231 (1964)] and 7.2 g of 2-[(2,2-dimethyl-1,3-dioxolan-4-yl)-methoxy]-acetic acid hydrazide in 80 ml of absolute ethanol is boiled under reflux for 25 hours. The reaction mixture is evaporated under reduced pressure and the resulting crude product is worked up by the process described in Example 1. This gives 8-chloro-1-(2,3-dihydroxy-propoxymethyl)-6-phenyl-4H-s-triazolo[4,3-a][1,4]benzodiazepine, which has a melting point of 130°–134° after recrystallisation from ethyl acetate.

EXAMPLE 5

A solution of 6.42 g (0.020 mol) of 7-chloro-5-(o-chlorophenyl)-2-mercapto-3H-1,4-benzodiazepine [c.f. Archer and Sternbach, J. Org. Chem., Volume 29, page 231 (1964)] and 4.26 g (0.0221 mol) of crude 3,6,9-trioxa-decanoic acid hydrazide in 65 ml of n-butanol is boiled under reflux for 16 hours. The reaction mixture is evaporated and the evaporation residue is chromatographed on 160 g of silica gel, particle size 0.063–0.2 mm, using ethyl acetate/methanol (10:1). The fractions containing a single compound are combined and evaporated and the product is crystallised from ether/petroleum ether. This gives 8-chloro-6-(o-chlorophenyl)-1-(2,5,8-tri-oxa-nonyl)-4H-s-triazolo[4,3-a][1,4]benzodiazepine which has a melting point of 115°–116°.

3,6,9-Trioxa-decanoic acid hydrazide, which is used as the starting material, can be prepared as follows:

Analogously to Example 8, crude ethyl 3,6,9-tri-oxa-decanoate, which has a boiling point of 67°–71°/0.03 mm Hg, is obtained from 12.0 g (0.1 mol) of diethylene glycol monomethyl ether and 11.4 g (0.1 mol) of ethyl diazoacetate.

Analogously to Example 8, crude 3,6,9-trioxa-decanoic acid hydrazide, which can be used without further purification, is obtained from 10.0 g (0.0485 mol) of ethyl 3,6,9-trioxa-decanoate and 4.85 g (0.097 mol) of hydrazine hydrate.

EXAMPLE 6

Analogously to Example 5, 8-chloro-6-phenyl-1-(2,5,8-trioxa-nonyl)-4H-s-triazolo[4,3-a][1,4]benzodiazepine is obtained from 5.73 g (0.020 mol) of 7-chloro-2-mercapto-5-phenyl-3H-1,4-benzodiazepine and 4.26 g (0.0221 mol) of crude 3,6,9-trioxa-decanoic acid hydrazide, and after crystallisation from ethyl acetate/petroleum ether this product has a melting point of 91°–93°.

EXAMPLE 7

Analogously to Example 5, 8-chloro-6-(o-chlorophenyl)-1-[(2,2-dimethyl-1,3-dioxolan-4-yl)-methoxymethyl]-4H-s-triazolo[4,3-a][1,4]benzodiazepine is obtained from 34.7 g (0.108 mol) of 7-chloro-5-(o-chlorophenyl)-2-mercapto-3H-1,4-benzodiazepine and 26.5 g (0.130 mol) of 2-[(2,2-dimethyl-1,3-dioxolan-4-yl)-methoxy]-acetic acid hydrazide in 350 ml of n-butanol after boiling under reflux for 20 hours and subsequent chromatography on 600 g of silica gel (eluant: ethyl acetate/methanol (10:1)), and after crystallisation from ethyl acetate/petroleum ether this product has a melting point of 149°–150°.

(a) A solution of 30.0 g (0.0634 mol) of 8-chloro-6-(o-chlorophenyl)-1-[(2,2-dimethyl-1,3-dioxolan-4-yl)-methoxy-methyl]-4H-s-triazolo[4,3-a][1,4]benzodiazepine in 600 ml of 90% strength aqueous acetic acid is warmed at 100°–105° for one hour. The reaction mixture is then evaporated in a rotary evaporator. In order to hydrolyse a little O-acetyl derivative which has formed, the evaporation residue is stirred with 400 ml of 1 N NaOH and 300 ml of ethanol. The ethanol is then distilled off in the rotary evaporator and the residual aqueous phase is extracted with methylene chloride. The organic phase is washed with water, dried over magnesium sulphate and evaporated. The residue is crystallised from ethyl acetate/isopropanol and 8-chloro-6-(o-chlorophenyl)-1-(2,3-dihydroxy-propoxy-methyl)-4H-s-triazolo[4,3-a][1,4]benzodiazepine with a melting point of 153°–155° is then obtained.

EXAMPLE 8

Analogously to Example 5, 8-chloro-6-(o-chlorophenyl)-1-(2,5,8,11-tetra-oxa-dodecyl)-4H-s-triazolo[4,3-a][1,4]benzodiazepine is obtained in the form of a slightly brown syrup from 17.0 g (0.053 mol) of 7-chloro-5-(o-chlorophenyl)-2-mercapto-3H-1,4-benzodiazepine and 17.4 g (0.074 mol) of 3,6,9,12-tetra-oxa-tridecanoic acid hydrazide in 170 ml of n-butanol (boiling under reflux for 18 hours), after chromatography on 600 g of silica gel (eluant: ethyl acetate/isopropanol (7:2)).

3,6,9,12-Tetra-oxa-tridecanoic acid hydrazide, which is used as the starting material, can be prepared as follows:

A solution of 50.0 g (0.304 mol) of triethylene glycol monomethyl ether in 500 ml of cyclohexane is heated to the reflux temperature. About 4 g of copper powder are added and a solution of 32 ml (34.88 g; 0.30 mol) of ethyl diazoacetate in 30 ml of cyclohexane is then added in the course of 45 minutes. After the addition is complete, the mixture is stirred under reflux for a further 3 hours. Subsequently it is cooled and filtered and the filtrate is evaporated in a rotary evaporator. The oily residue is distilled in vacuo. According to analysis by gas chromatography, the fraction which boils at 70°–116°/0.1 mm Hg contains about 80% of ethyl 3,6,9,12-tetra-oxatridecanoate and about 15% of triethylene glycol monomethyl ether. This material is further processed without further purification.

A solution of 61 g (0.244 mol) of crude ethyl 3,6,9,12-tetra-oxa-tridecanoate and 25 ml (0.488 mol) of hydrazine hydrate in 600 ml of ethanol is left to stand for 25 hours at 25°. The reaction mixture is evaporated and the crude, oily 3,6,9,12-tetra-oxa-tridecanoic acid hydrazide, which is thus obtained, is further processed direct.

EXAMPLE 9

Tablets containing 5 mg of 8-chloro-1-(2-hydroxyethoxy-methyl)-6-phenyl-4H-s-triazolo[4,3-a][1,4]benzodiazepine can be prepared as follows:

| Composition (for 10,000 tablets): | |
|---|---|
| 8-chloro-1-(2-hydroxyethoxy-methyl)-6-phenyl-4H-s-triazolo[4,3-a][1,4]benzodiazepine | 50.0 g |
| lactose | 550.0 g |
| potato starch | 352.0 g |
| gelatine | 8.0 g |
| talc | 60.0 g |
| magnesium stearate | 10.0 g |
| silicon dioxide (highly disperse) | 20.0 g |
| ethanol | q.s |

The 8-chloro-1-(2-hydroxyethoxy-methyl)-6-phenyl-4H-s-triazolo[4,3-a][1,4]benzodiazepine is mixed with the lactose and 292 g of potato starch and the mixture is moistened with an ethanolic solution of 8 g of gelatine and granulated through a sieve. After drying, 60 g of potato starch, the talc, the magnesium stearate and the silicon dioxide are mixed in and the mixture is pressed to give tablets which each weigh 105 mg and, if desired, can be provided with breaking grooves for finer adjustment of the dosage.

EXAMPLE 10

Dragées containing 2.5 mg of 8-chloro-1-(2-hydroxyethoxy-methyl)-6-phenyl-4H-s-triazolo[4,3-a][1,4]benzodiazepine can be prepared as follows:

| Composition (for 1,000 dragees): | |
|---|---|
| 8-chloro-1-(2-hydroxyethoxy-methyl)-6-phenyl-4H-s-triazolo[4,3-a][1,4]benzodiazepine | 2.50 g |
| maize starch | 32.00 g |
| silicon dioxide (highly disperse) | 8.00 g |
| stearic acid | 2.00 g |
| ethylcellulose | 6.00 g |
| stearin | 6.00 g |
| talc | 41.00 g |
| magnesium stearate | 2.00 g |
| gum arabic | 7.50 g |
| dye | 0.15 g |
| sugar | 53.35 g |
| isopropanol | q.s. |
| water | q.s. |

The 8-chloro-1-(2-hydroxyethoxy-methyl)-6-phenyl-4H-s-triazolo[4,3-a][1,4]benzodiazepine is mixed well with 16 g of maize starch and 6 g of the silicon dioxide and the mixture is moistened with a solution of the stearic acid, the ethyl-cellulose and the stearin in about 70 ml of isopropanol and granulated through a III sieve (Ph. Helv. V). The granules are dried for about 14 hours and then pushed through a III-IIIa sieve. The granules are then mixed with 16 g of maize starch, 16 g of talc and the magnesium stearate and the mixture is pressed to give 1,000 dragée cores. These are coated with a concentrated aqueous syrup of the gum arabic, the dye, 2 g of the silicon dioxide, 25 g of the talc and the sugar and dried. The weight of the dragées is 160.5 mg.

EXAMPLE 11

Suppositories containing 10 mg of 8-chloro-1-(2-hydroxyethoxy-methyl)-6-phenyl-4H-s-triazolo[4,3-a][1,4]benzodiazepine can be prepared as follows:

| Composition (for 1,000 suppositories): | |
|---|---|
| 8-chloro-1-(2-hydroxyethoxy-methyl)-6-phenyl-4H-s-triazolo[4,3][1,4]benzodiazepine | 10.0 g |
| suppository base (for example cacao butter) | 1,990.0 g |

The 8-chloro-1-(2-hydroxyethoxy-methyl)-6-phenyl-4H-s-triazolo[4,3-a][1,4]benzodiazepine and the finely ground suppository base are mixed thoroughly and the mixture is then melted. Suppositories weighing 2 g are cast from the melt, which is kept homogeneous by stirring.

What we claim is:

1. An etherified diazepine derivative of the formula

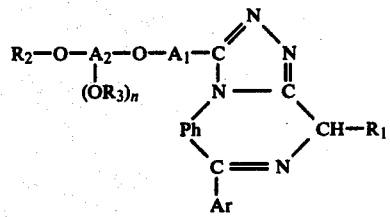

in which $R_1$ represents hydrogen or alkyl having up to 3 carbon atoms, $R_2$ and $R_3$ independently of one another each represent hydrogen or alkyl having up to 7 carbon atoms, or represent the partial formula $R_4$—(OCH$_2$—CH$_2$)$_m$, in which $R_4$ represents hydrogen or alkyl having up to 7 carbon atoms and m represents the number 1 to 3, $A_1$ represents alkylidene or alkylene having up to 3 carbon atoms, $A_2$, depending on the meaning of n, represents alkylene or alkanetriyl having 2 to 5 carbon atoms, no carbon atom in the radical $A_2$ being bonded to more than one oxygen atom, n represents the number 0 or 1, Ph represents 1,2-phenylene which is unsubstituted or substituted in 8-position by lower alkyl, lower alkoxy, halogen having an atomic number up to and including 35, or trifluoromethyl, and Ar represents phenyl which is unsubstituted or substituted by lower alkyl, lower alkoxy, halogen having an atomic number of up to and including 35, or trifluoromethyl in o-position.

2. A compound of the formula I according to claim 1, in which $R_1$ represents hydrogen, $R_2$ and $R_3$ independently of one another each represent hydrogen or alkyl having up to 3 carbon atoms, or $R_2$ represents the partial formula $R_4$—(OCH$_2$—CH$_2$)$_m$—, in which $R_4$ represents alkyl having up to 3 carbon atoms, $A_1$ represents methylene , n represents 0 or 1, $A_2$ represents ethylene if n represents 0, or represents 1,2,3-propanetriyl if n represents 1, Ph represents 1,2-phenylene, which is unsubstituted or substituted by halogen, and Ar represents phenyl which is unsubstituted or substituted by halogen.

3. A compound of the formula I according to claim 1, in which $R_1$ represents hydrogen, $R_2$ and $R_3$ independently of one another each represent hydrogen or alkyl having up to 3 carbon atoms, or $R_2$ represents the partial formula $R_4$—(OCH$_2$—CH$_2$)$_m$—, in which $R_4$ represents alkyl having up to 3 carbon atoms, $A_1$ represents methylene, n represents 0 or 1, $A_2$ represents ethylene if n represents 0, or represents 1,2,3-propanetriyl if n represents 1, Ph represents 1,2-phenylene which is substituted by chlorine, and Ar represents phenyl which is unsubstituted or substituted in the 2-position by chlorine or fluorine.

4. A 1-(2-$R_2$-O-ethoxy-methyl)-6-(2-R-phenyl)-8-chloro-4H-s-triazolo[4,3-a][1,4]benzodiazepine, in which $R_2$ represents hydrogen or methyl and R represents hydrogen, fluorine or chlorine.

5. A 1-(2,3-dihydroxy-propoxy-methyl)-6-(2-R-phenyl)-8-chloro-4H-s-triazolo[4,3-a][1,4]benzodiazepine, in which R represents hydrogen, fluorine or chlorine.

6. 8-Chloro-1-(2-hydroxyethoxy-methyl)-6-phenyl-4H-s-triazolo[4,3-a][1,4]benzodiazepine.

7. 8-Chloro-1-(2,3-dihydroxypropoxy-methyl)-6-phenyl-4H-s-triazolo[4,3-a][1,4]benzodiazepine.

8. 8-Chloro-6-(o-chlorophenyl)-1-(2,5,8-tri-oxa-nonyl)-4H-s-triazolo[4,3-a][1,4]benzodiazepine.

9. 8-Chloro-6-phenyl-1-(2,5,8-trioxa-nonyl)-4H-s-triazolo[4,3-a][1,4]benzodiazepine.

10. 8-Chloro-6-(o-chlorophenyl)-1-[(2,2-dimethyl-1,3-dioxolan-4-yl)-methoxy-methyl]-4H-s-triazolo[4,3-a][1,4]-benzodiazepine.

11. 8-Chloro-6-(o-chlorophenyl)-1-(2,3-dihydroxypropoxymethyl)-4H-s-triazolo[4,3-a][1,4]benzodiazepine.

12. 8-Chloro-6-(o-chlorophenyl)-1-(2,5,8,11-tetra-oxa-dodecyl)-4H-s-triazolo[4,3-a][1,4]benzodiazepine.

13. A pharmaceutical composition useful in the treatment of states of epilepsy, stress and agitation in a warm-blooded animal, comprising a therapeutically effective amount of a compound according to claim 1, which corresponds to the formula

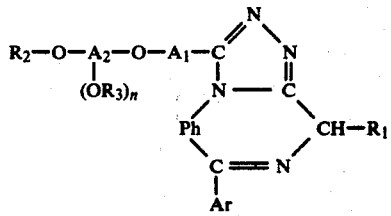

in which $R_1$ represents hydrogen or alkyl having up to 3 carbon atoms, $R_2$ and $R_3$ independently of one another each represent hydrogen or alkyl having up to 7 carbon atoms, or represent the partial formula $R_4$—(OCH$_2$—CH$_2$)$_m$—, in which $R_4$ represents hydrogen or alkyl having up to 7 carbon atoms and m represents the number 1 to 3, $A_1$ represents alkylidene or alkylene having up to 3 carbon atoms, $A_2$, depending on the meaning of n, represents alkylene or alkanetriyl having 2 to 5 carbon atoms, no carbon atom in the radical $A_2$ being bonded to more than one oxygen atom, n represents the number 0 or 1, Ph represents 1,2-phenylene which is unsubstituted or substituted in 8-position by lower alkyl, lower alkoxy, halogen having an atomic number up to and including 35, or trifluoromethyl, and Ar represents phenyl which is unsubstituted or substituted by lower alkyl, lower alkoxy, halogen having an atomic number of up to and including 35, or trifluoromethyl in o-position, or an addition salt thereof, together with a pharmaceutical carrier.

14. A pharmaceutical composition of claim 13, wherein a compound of the formula I given in claim 13 is present, in which $R_1$ represents hydrogen, $R_2$ and $R_3$ independently of one another each represent hydrogen or alkyl having up to 3 carbon atoms, or $R_2$ represents said partial formula $R_4$—(OCH$_2$—CH$_2$)$_m$—, in which $R_4$ represents alkyl having up to 3 carbon atoms, $A_1$ represents methylene, n represents 0 or 1, $A_2$ represents ethylene is n represents 0, or represents 1,2,3-propanetriyl if n represents 1.

15. A pharmaceutical composition of claim 13, wherein a compound of the formula I given in claim 13 is present, in which $R_1$ represents hydrogen, $R_2$ and $R_3$ independently of one another each represent hydrogen or alkyl having up to 3 carbon atoms, or $R_2$ represents the partial formula $R_4$—(OCH$_2$—CH$_2$)$_m$—, in which $R_4$ represents alkyl having up to 3 carbon atoms, $A_1$ represents methylene, n represents 0 or 1, $A_2$ represents ethylene if n represents 0, or represents 1,2,3-propanetriyl if n represents 1, Ph represents 1,2-phenylene which is substituted by chlorine, and Ar represents phenyl which is unsubstituted or substituted in the 2-position by chlorine or fluorine.

16. A pharmaceutical composition according to claim 13 wherein a 1-(2-$R_2$-O-ethoxy-methyl)-6-(2-R-phenyl)-8-chloro-4H-s-triazolo[4,3-a][1,4]benzodiazepine is present, in which $R_2$ represents hydrogen or methyl and R represents hydrogen, fluorine or chlorine.

17. A pharmaceutical composition according to claim 13, wherein a 1-(2,3-dihydroxy-propoxy-methyl)-6-(2-R-phenyl)-8-chloro-4H-s-triazolo[4,3-a][1,4]benzodiazepine is pesent, in which R represents hydrogen, fluorine or chlorine.

18. A pharmaceutical composition according to claim 13, wherein 8-Chloro-1-(2-hydroxyethoxy-methyl)-6-phenyl-4H-s-triazolo[4,3-a][1,4]benzodiazepine is present.

19. A pharmaceutical composition according to claim 13, wherein 8-Chloro-1-(2,3-dihydroxypropoxy-methyl)-6-phenyl-4H-s-triazolo[4,3-a][1,4]benzodiazepine is present.

20. A pharmaceutical composition according to claim 13, wherein 8-Chloro-6-(o-chlorophenyl)-1-(2,5,8-tri-oxa-nonyl)-4H-s-triazolo[4,3-a][1,4]benzodiazepine is present.

21. A pharmaceutical composition according to claim 13, wherein 8-Chloro-6-phenyl-1-(2,5,8-trioxa-nonyl)-4H-s-triazolo[4,3-a][1,4]benzodiazepine is present.

22. A pharmacuetical composition according to claim 13 wherein 8-Chloro-6-(o-chlorophenyl)-1-(2,3-dihydroxy-propoxy-methyl)-4H-s-triazolo[4,3-a][1,4]benzodiazepine is present.

23. A pharmaceutical composition according to claim 13, wherein 8-Chloro-6-(o-chlorophenyl)-1-(2,5,8,11-tetra-oxa-dodecyl)-4H-s-triazolo[4,3-a][1,4]benzodiazepine is present.

24. A method for the treatment of states of epilepsy, stress and agitation in a warm-blooded animal, comprising administration to said animal of a therapeutically effective amount of a compound according to claim 1, which corresponds to the formula I given in claim 1, or of a pharmacologically acceptable acid addition salt thereof.

25. A method according to claim 24 comprising administration of a therapeutically effective amount of 1-(2-$R_2$-O-ethoxy-methyl)-6-(2-R-phenyl)-8-chloro-4H-s-triazolo[4,3-a][1,4]benzodiazepine, in which $R_2$ represents hydrogen or methyl and R represents hydrogen, fluorine or chlorine.

26. A method according to claim 24 comprising administration of a therapeutically effective amount of 1-(2,3-dihydroxy-propoxy-methyl)-6-(2-R-phenyl)-8-chloro-4H-s-triazolo[4,3-a][1,4]benzodiazepine, in which R represents hydrogen, fluorine or chlorine.

27. A method according to claim 24 comprising administration of a therapeutically effective amount of 8-Chloro-1-(2-hydroxyethoxy-methyl)-6-phenyl-4H-s-triazolo[4,3-a][1,4]benzodiazapine.

28. A method according to claim 24 comprising administration of a therapeutically effective amount of 8-Chloro-1-(2,3-dihydroxypropoxy-methyl)-6-phenyl-4H-s-triazolo[4,3-a][1,4]benzodiazepine.

29. A method according to claim 24 comprising administration of a therapeutically effective amount of 8-Chloro-6-(o-chlorophenyl)-1-(2,5,8-tri-oxa-nonyl)-4H-s-triazolo [4,3-a][1,4]benzodiazepine.

30. A method according to claim 24 comprising administration of a therapeutically effective amount of 8-Chloro-6-phenyl-1-(2,5,8-trioxa-nonyl)-4H-s-triazolo[4,3-a][1,4]benzodiazepine.

31. A method according to claim 24 comprising administration of a therapeutically effective amount of 8-Chloro-6-(o-chlorophenyl)-1-(2,3-dihydroxy-propoxymethyl)-4H-s-triazolo[4,3-a][1,4]benzodiazepine.

32. A method according to claim 24 comprising administration of a therapeutically effective amount of 8-Chloro-6-(o-chlorophenyl)-1-(2,5,8,11-tetra-oxa-dodecyl)-4H-s-triazolo[4,3-a][1,4]benzodiazepine.

* * * * *